(12) United States Patent
Takamoto et al.

(10) Patent No.: US 7,150,742 B2
(45) Date of Patent: Dec. 19, 2006

(54) GRAFT GRASPING DEVICE

(75) Inventors: Shinichi Takamoto, Tokyo-to (JP);
Yoshihiro Suematsu, Tokyo-to (JP);
Hiroaki Tanabe, Tokyo-to (JP);
Hideaki Kataoka, Osaka (JP); Katsuya Miyagawa, Osaka (JP); Akifumi Yoneda, Osaka (JP)

(73) Assignee: Nipro Corporation, Osaka (JP)

( * ) Notice: Subject to any disclaimer, the term of this patent is extended or adjusted under 35 U.S.C. 154(b) by 203 days.

(21) Appl. No.: 10/695,460

(22) Filed: Oct. 29, 2003

(65) Prior Publication Data
US 2004/0138649 A1    Jul. 15, 2004

(30) Foreign Application Priority Data
Oct. 30, 2002  (JP)  ............................. 2002-315449
Aug. 26, 2003  (JP)  ............................. 2003-300723

(51) Int. Cl.
*A61B 17/00* (2006.01)
(52) U.S. Cl. ............................ 606/1; 606/205; 128/899
(58) Field of Classification Search .................... 606/1, 606/108, 114, 115, 123, 151, 153, 157, 205; 128/899
See application file for complete search history.

(56) References Cited

U.S. PATENT DOCUMENTS

| 3,561,448 A | 2/1971 | Peternel ...................... 128/334 |
| 4,350,160 A | 9/1982 | Kolesov et al. ......... 128/334 R |
| 4,651,733 A | 3/1987 | Mobin-Uddin .......... 128/303 R |
| 6,024,748 A | 2/2000 | Manzo et al. ................ 606/153 |
| 6,375,651 B1 * | 4/2002 | Grasso et al. .................. 606/15 |
| 2002/0038100 A1 | 3/2002 | Okada ........................... 604/8 |

FOREIGN PATENT DOCUMENTS

| EP | 0 993 806 A2 | 4/2000 |
| JP | 2001-37762 A | 2/2001 |
| JP | 2001-190557 A | 7/2001 |
| JP | 2002-95666 A | 4/2002 |
| JP | 2002-360593 A | 12/2002 |

* cited by examiner

*Primary Examiner*—Michael J. Hayes
*Assistant Examiner*—Michael G. Mendoza
(74) *Attorney, Agent, or Firm*—Kubovcik & Kubovcik

(57) ABSTRACT

A graft grasping device includes a graft grasping member including a soft tubular grasping portion having a substantially C-shaped cross section and a suction tube which communicates with a lumen of the grasping portion and is connected to a side wall of the grasping portion. A recessed portion including at least a communication port which communicates with a lumen of the suction tube and the lumen of the grasping portion is formed on an inner wall of the grasping portion. The recessed portion is covered with a porous sheet and a mesh sheet is interposed between the recessed portion and the porous sheet.

7 Claims, 12 Drawing Sheets

GRAFT GRASPING DEVICE

BACKGROUND OF THE INVENTION

1. Field of the Invention

The present invention relates to a graft grasping device. More specifically, the present invention relates to a graft grasping device capable of grasping by negative pressure a graft having an open anastomosing port during coronary artery bypass grafting.

2. Description of the Related Art

In order to treat ischemic heart diseases such as angina pectoris and myocardial infarct, percutaneous transluminal coronary angioplasty (PTCA) and coronary artery bypass grafting (CABG) are carried out. Of these, PTCA, which is not highly invasive, has been very popular in recent years. However, CABG is suitably selected for patients having a lesion in the left main coronary artery, patients having a lesion in the 3 major ramuses, and patients who suffer from restenosis very often after PTCA. Currently, CABG is carried out on about 15,000 patients a year in Japan and about 10 times more patients in Europe and the US.

CABG, in which part of an autograft such as a great saphenous vein is used as a bypass graft under general anesthesia, is carried out by a surgeon. More specifically, one end of the bypass graft is sutured with the aorta and the other end is sutured with a region after the stenosis portion of the coronary artery. After CABG, the blood bypasses the stenosis portion and runs from the aorta to the myocardium through the newly transplanted bypass graft.

When the bypass graft is anastomosed with the aorta or the coronary artery, it must be grasped while its anastomosing port is open. Therefore, a pair of tweezers or the like has been conventionally used. However, grasping with tweezers or the like may damage the intima of the bypass graft. This is because the ends of the tweezers contact the intima of the graft. Also, most of the tweezers or the like are made from a hard material such as a metal and are made uneven to prevent slipping. Thus, there is a fear that the intima of the graft may be further damaged. When the intima of the bypass graft is damaged, the adhesion of a thrombus to the damaged part or intimal thickening may occur, thereby increasing the possibility of restenosis occurring. When restenosis occurs, a surgical operation is needed again, thereby increasing a burden on a patient. Also, in the case where only part of the anastomosing port is grasped with the tweezers, the anastomosing port of the bypass graft cannot be opened wide.

In view of the above, a graft grasping device in which a bypass graft is suction-grasped by a grasping portion composed of a circular hollow tube in the form of a ring having a plurality of suction ports in the inner portion of the ring has been proposed for use in place of the conventional tweezers (see Japanese laid-open publication No. JP 2002-360593 A).

However, since the graft grasping device of said invention has a grasping portion that is a ring formed from a circular hollow tube, when the bypass graft is suction-grasped, the contact area between the grasping portion and the graft is small, causing a fear that the graft may be separated from the grasping portion by a small force during a surgical operation. That is, when sufficiently high ease of operation is to be obtained while the graft is grasped, the contact area between the grasping portion and the graft must be large. Also, to insert a graft having almost the same diameter as the inner diameter of the grasping portion, the grasping portion must be opened wide. To open the grasping portion wide, the grasping portion must be made from a material having sufficiently high flexibility. However, when such a soft flexible material is used for the grasping portion, the grasping portion may be crushed by a suction force, causing a fear that the bypass graft may not be suction-grasped. The graft grasping device of JP 2002-360593 A is not provided with means for preventing the crushing of the grasping portion. Further, the anastomosing port of a bypass graft is cut obliquely in most cases to ensure a flow of blood. To suction-grasp this bypass graft, it must be grasped at a position away from the end of the anastomosing port. In this case, there is another fear that the anastomosing port may not be opened wide.

As a result of earnest investigations made by the inventors to solve the problems associated with the conventional techniques, the present invention has been completed.

An object of the present invention is to open an anastomosing port of a bypass graft to an anastomosing region without causing damage to an intima during a bypass operation.

BRIEF SUMMARY OF THE INVENTION

The above-mentioned object and other objects of the present invention will be further clarified in the following description, and these objects are attained by the present invention which comprises the constitution described below.

That is, the present invention relates to:

(1) a graft grasping device, including a graft grasping means that grasps a graft in a lumen softly and includes a soft tubular-shaped member capable of expanding a diameter of the lumen easily, and a suction force transmission means which communicates with the lumen of the graft grasping means, in which, while a graft is held in the lumen, a suction force transmitted from the suction force transmission means widely acts on an inside of the lumen;

(2) A graft grasping device according to (1) above, including:

a graft grasping member including a soft tubular-shaped grasping portion having a substantially C-shaped cross section perpendicular to the axis of the tubular-shaped grasping portion and a slit in the longitudinal (axial) direction; and a suction tube communicating with the lumen of the grasping portion and connected to an outer wall of the grasping portion, in which:

an inner wall of the grasping portion has at least a recessed portion including a portion communicating with a lumen of the suction tube;

the recessed portion is covered with a sheet having a plurality of pores; and a mesh sheet is present in a space defined between the recessed portion and the sheet.

(3) A graft grasping device according to (2) above, in which the recessed portion is formed on the entire inner wall excluding portions adjacent to a distal end and a proximal end of the grasping portion and portions adjacent to the slit.

(4) A graft grasping device according to (2) above, in which at least one end face of the grasping portion is formed obliquely with respect to the longitudinal direction of the grasping portion.

(5) A graft grasping device according to any one of (2) to (4) above, in which the device is provided with a grip.

(6) A graft grasping device according to (5) above, in which the grip is connected to a suction tube connection portion provided on the outer wall of the grasping portion concentrically with the suction tube.

(7) A graft grasping device according to any one of (2) to (6) above, in which a connector is provided at a proximal end of the suction tube.

DETAILED DESCRIPTION OF THE INVENTION

Figure 1:
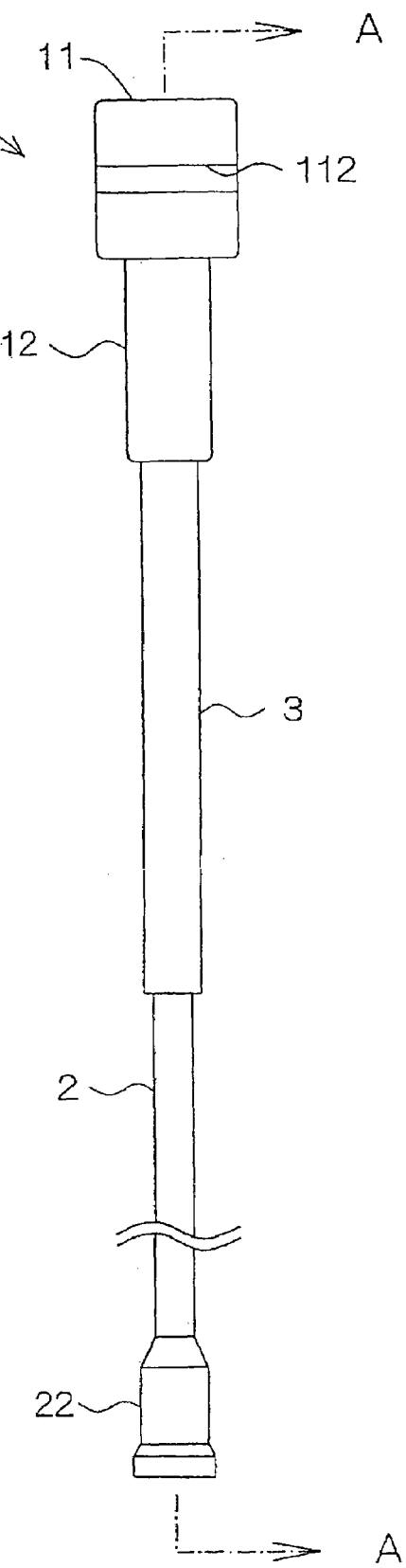
FIG. 1 is a front view of an embodiment of the present invention.

Embodiments of the present invention will be described hereinbelow with reference to the accompanying drawings.

As shown in FIGS. 1 to 5, the graft grasping device of the present invention includes a graft grasping member 1 including a soft tubular-shaped grasping portion 11 having a substantially C-shaped cross section and a suction tube 2 which communicates with a lumen 111 of the grasping portion 11 and is connected to an outer wall 31 of the grasping portion 11. A recessed portion 114 including at least a communication port 113 which communicates with a lumen 21 of the suction tube 2 and the lumen 111 of the grasping portion 11 is formed on an inner wall 32 of the grasping portion 11. The recessed portion 114 is covered with a porous sheet 13 and a mesh sheet 14 is interposed between the recessed portion 114 and the porous sheet 13.

Figure 2:
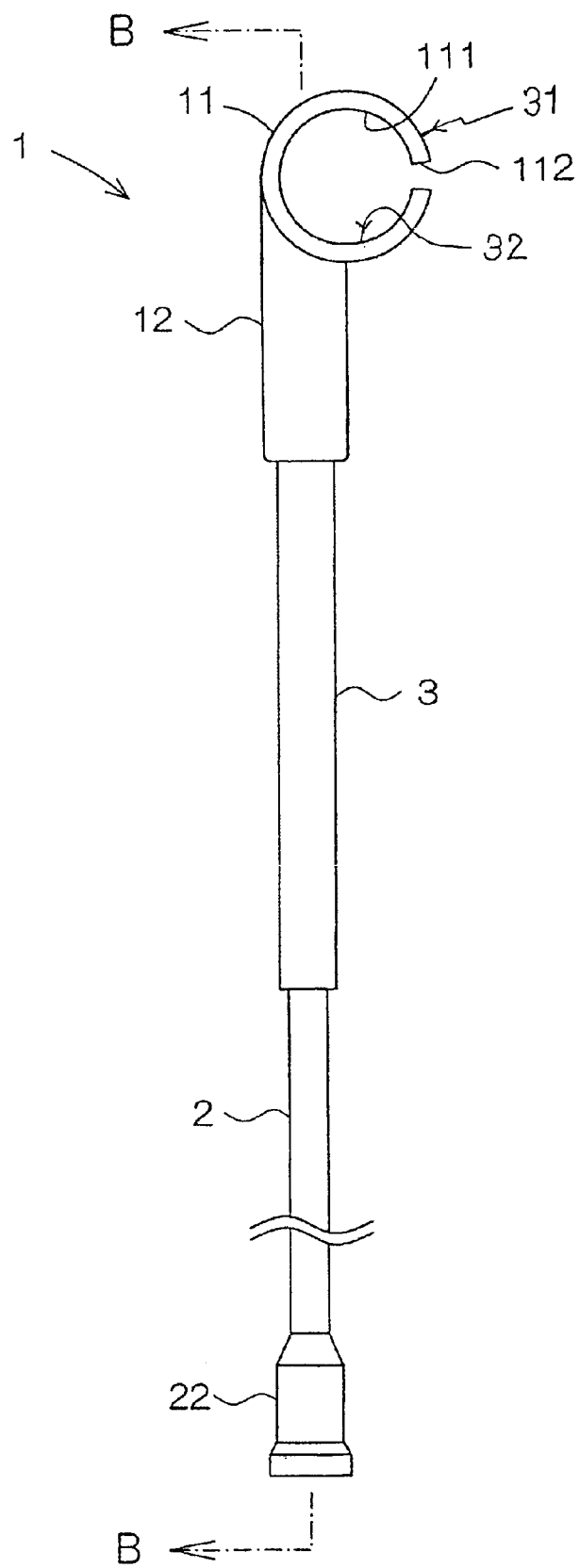
FIG. 2 is a left side view of FIG. 1.
Figure 3:
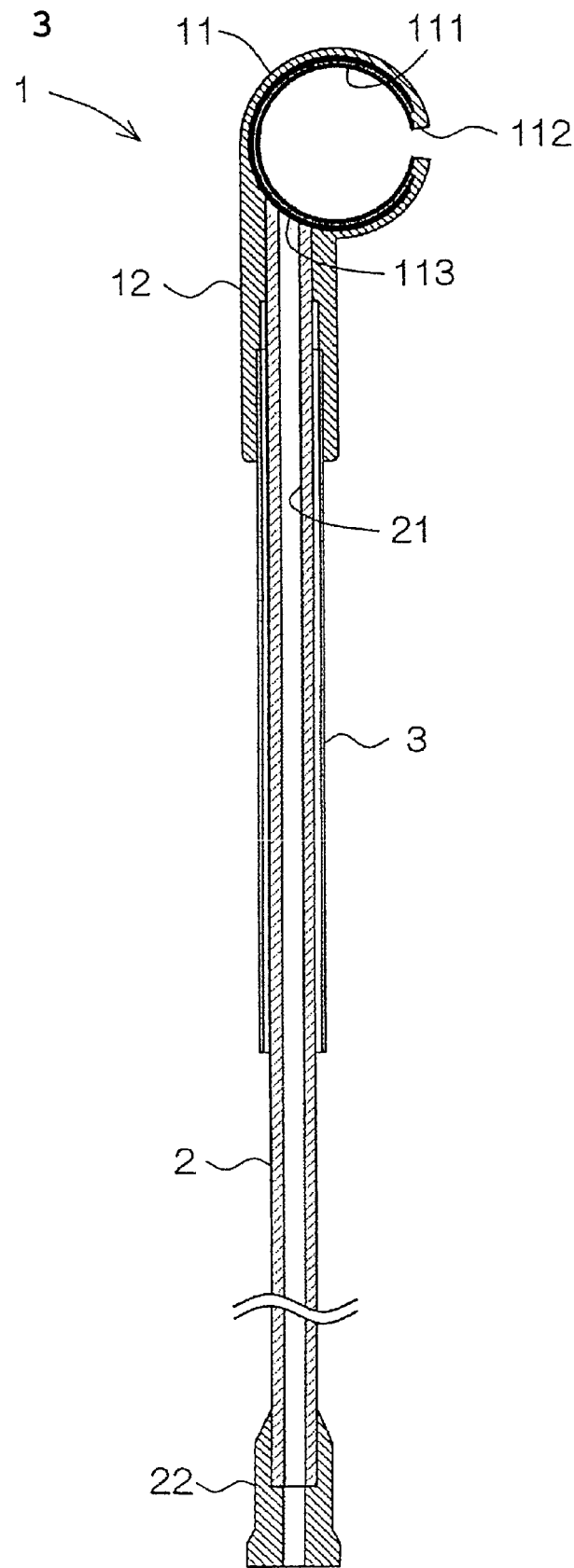
FIG. 3 is a cross sectional view of FIG. 1 along line A—A.

As shown in FIGS. 1 and 2, the graft grasping member 1 includes a grasping portion 11 which functions as graft grasping means. The grasping portion 11 is a soft tubular-shaped member having a slit 112 in the longitudinal, or axial, direction and has a lumen 111 for softly grasping a graft. The lumen 111 has a substantially C-shaped cross sectional form due to the formation of the slit 112. The grasping portion 11 can be easily expanded in diameter by the slit 112 so that the graft can be attached to and detached from the grasping portion 11 by opening the slit 112 before and after the anastomosis of the graft. The slit may be formed at a position where it forms a substantially right angle with the installation angle of a suction tube or a grip to be described hereinafter or may be formed at a position symmetrical thereto. As a result, when the suction tube or grip is pulled, the grasping portion can be thereby easily removed from the graft.

A communication port 113 which is a portion communicating with the lumen 21 of the suction tube 2 is formed in the grasping portion 11. The communication port 113 is provided with a suction tube connection portion 12 projecting from the grasping portion 11. The suction tube connection portion 12 is connected to the suction tube 2. The suction tube connection portion 12 may be connected concentrically to a grip 3 around the suction tube 2, if necessary, when a hand of an operator is hard to insert, for example, behind the heart.

Figure 4:
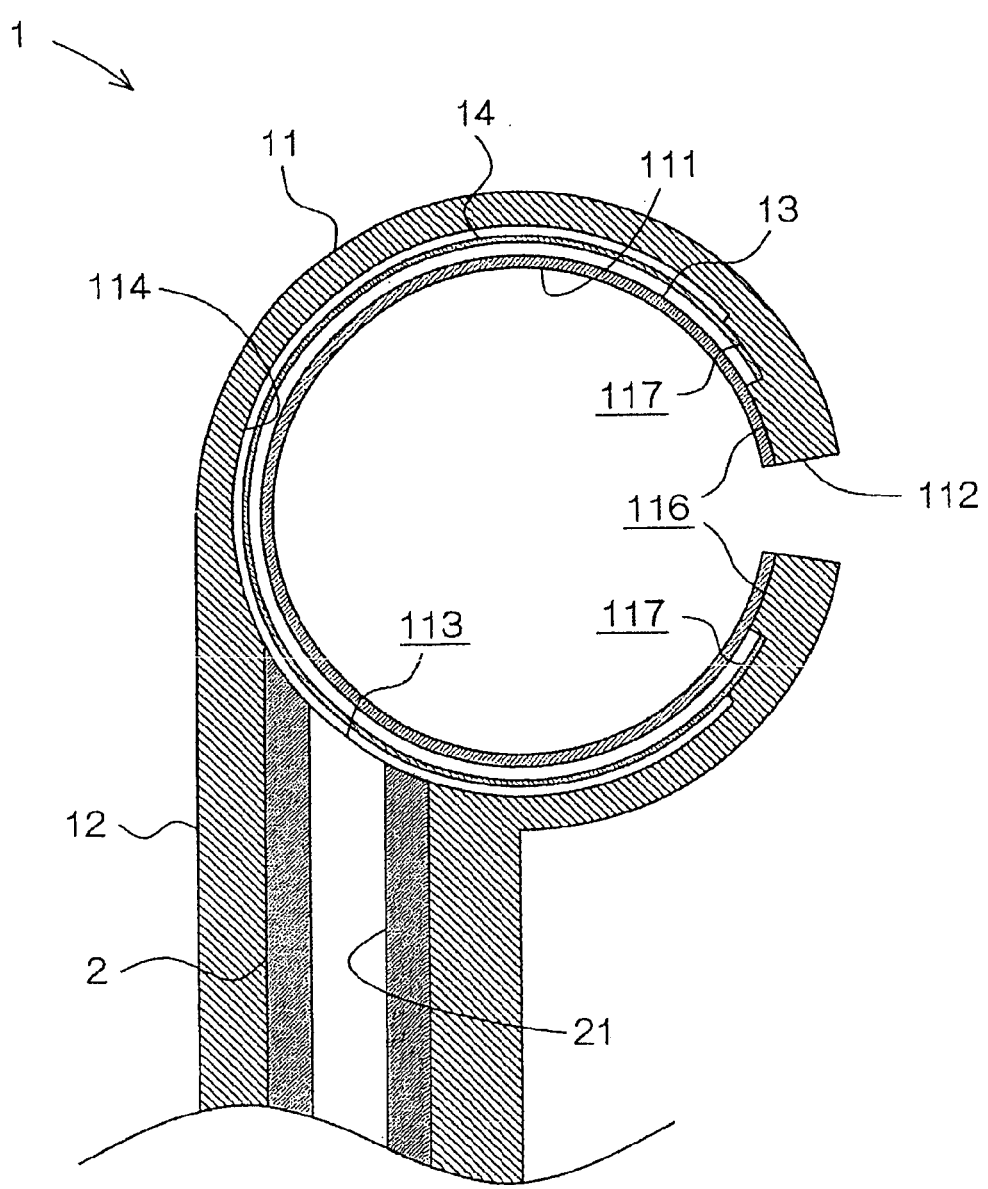
FIG. 4 is an enlarged view of a main portion of FIG. 3.
Figure 5:
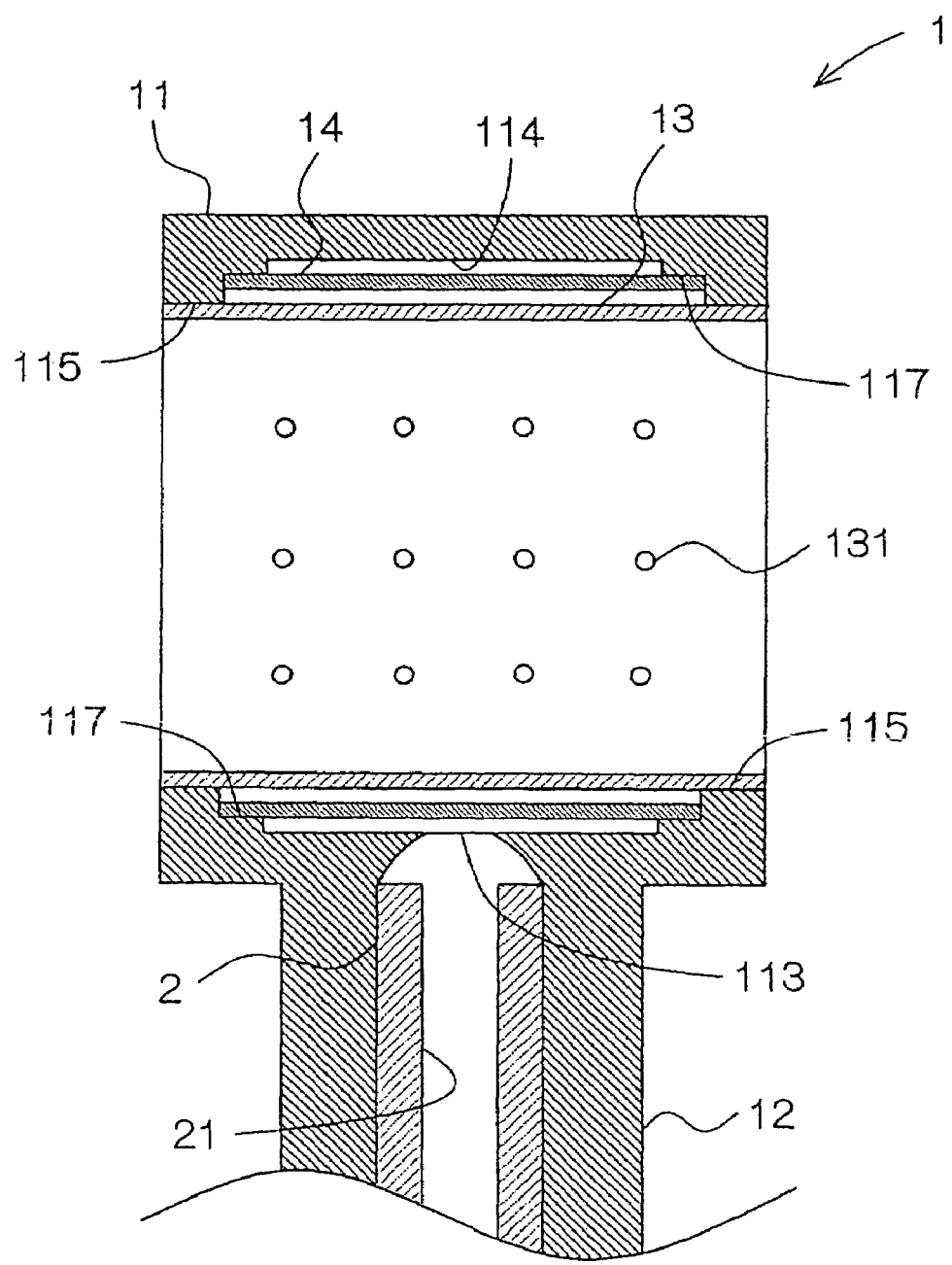
FIG. 5 is an enlarged cross sectional view of FIG. 2 along line B—B.

The grasping portion 11 is generally a tubular-shaped member made from a soft flexible resin such as polyurethane, polyethylene or silicone. As best shown in FIGS. 4 to 5, a recessed portion 114 includes at least the communication port 113 of the portion 11. The recessed portion 114 is covered with a porous sheet 13 having a plurality of pores 131 and a mesh sheet 14 is inserted into a space between the recessed portion 114 and the porous sheet 13. The length and inner diameter of the grasping portion 11 may be suitably selected according to the diameter of the graft to be used as a bypass. For example, the grasping portion 11 may have a length of about 10 mm and an inner diameter of about 5 mm.

It is preferable that the recessed portion 114 is formed in a large portion of the inner wall of the grasping portion 11 in order that the installation port of the bypass graft grasped by the graft grasping device to the anastomosing part opens wide. The recessed portion 114 is preferably formed in the entire inner wall excluding portions 115 adjacent to the distal and proximal ends of the grasping portion 11 and portions 116 adjacent to the slit 112 so that the suction force of the suction tube 2 acts on substantially the entire graft.

The porous sheet 13 is adhered to the inner wall of the grasping portion 11 with portions adjacent to the recessed portion 114 as a margin. In FIGS. 4 and 5, the portions 115 adjacent to the distal and proximal ends of the grasping portion 11 and the portions 116 adjacent to the slit 112 serve as the margin. The diameter and the number of pores 131 of the porous sheet 13 are not particularly limited if the suction force is widely transmitted to the lumen 111 through the pores 131 and the graft can be grasped softly and reliably. The diameter is suitably about 1 mm and the number of pores is suitably about 20 to 40. The material of the porous sheet 13 is not particularly limited if it can be adhered or welded to the grasping portion 11 and is preferably the same as the material of the grasping portion 11.

The mesh sheet 14 is formed from a material which can adhere to the grasping portion 11 and may be adhered or welded to the grasping portion 11 with stepped portions 117 formed adjacent to the margins 116 and the margins 115 as the margin as shown, for example, in FIGS. 4 and 5. Alternatively, the mesh sheet 14 may not be adhered to the grasping portion 11 but may be existent in the space between the recessed portion 114 and the porous sheet 13. The stepped portions 117 may be formed adjacent to one or both of the margins 116 and the margins 115.

When the graft is suction-grasped, there is a fear that the porous sheet 13 may be brought into close contact with the recessed portion 114 by a negative pressure generated between the lumen 111 and the porous sheet 13. In particular, when the porous sheet 13 is brought into close contact with the recessed portion 114 so as to fill up the communication port 113, there is a fear that, as the suction force is transmitted only through the pores 131 of the part of the porous sheet 13 corresponding to the communication port 113, a uniform suction force cannot be obtained and the anastomosing port (41 in FIG. 7) of the graft may not be opened. The mesh sheet 14 is a means for preventing the porous sheet 13 from being brought into close contact directly with the recessed portion 114 and for transmitting the suction force to the pores 131 of the porous sheet 13 other than at the part corresponding to the communication port 113 through the mesh. The material of the mesh sheet 14 can be the same as that of the grasping portion 11 and the porous sheet 13 as long as the mesh sheet allows the suction force to be transmitted to the pores of the porous sheet 13. However, the mesh sheet is preferably made of a material having a greater hardness that of the grasping portion and that is not crushed when suction is applied. A mesh sheet made of knitted nylon fibers is an example of a preferred mesh sheet 14.

According to the constitution including the recessed portion 114, the porous sheet 13, and the mesh sheet 14, while the graft (4 in FIG. 6) is held within the lumen 111 (not grasped yet), the suction force transmitted from the suction tube 2 widely acts on the inside of the lumen 111. That is, in this constitution, the wall of the lumen 111 of the grasping portion 11 is the inner surface of the porous sheet 13. While the graft (see 4 in FIG. 6) is held in the lumen 111, the suction force transmitted to the recessed portion 114 of the grasping portion 11 from the communication port 113 through the lumen 21 of the suction tube 2 widely acts on the inside of the lumen 111 through the mesh sheet 14 and the pores 131 of the porous sheet 13. Then, the graft is uniformly dilated by the transmitted suction force and adsorbed to the inner surface of the porous sheet 13 and put into a state of being grasped by the grasping portion 11.

The suction tube 2 is made from a flexible resin such as polyurethane, polyethylene, polyester, polypropylene, polyamide, soft polyvinyl chloride, fluororesin, or silicone. The distal end of the suction tube 2 is connected to the suction tube connection portion 12 of the graft grasping member 1 and the proximal end thereof is preferably provided with a connector 22 for connection to a suction device (not shown). A material of the connector 22 can be a synthetic resin such as polypropylene, ABS resin, polyvinyl chloride, polyethylene, polyethylene terephthalate, or polycarbonate. A metal bar having pseudo-elasticity may be buried in the wall of the suction tube. In this way, an operation can be performed while handling the suction tube and the tube can be fixed while it is curved so as not to interfere with a surgical operation.

The graft grasping member 1 may be provided with a grip 3 to make it easy to handle. Since the suction tube connection portion 12 may be used as a grip, the grip 3 is not always necessary. However, for example, when it is difficult to insert an operator's hand in the area of the grafting site, the grip is indispensable. The installation position and shape of the grip 3 are not particularly limited but the grip 3 is preferably formed in a tubular shape and connected to the suction tube connection portion 12 provided on the outer wall of the grasping portion 11 concentrically to the suction tube 2. The material for the grip 3 may be a metal such as stainless steel or brass. When flexibility is required for the grip 3, a synthetic resin similar to that of the grasping portion 11 such as polyurethane, polyester, polyethylene, polypropylene, polyamide, fluororesin, or silicone may be used, or a universal joint or flexible hose made of a rigid member such as a metal member may be used. The length of the grip 3 is not particularly limited but is preferably about 100 mm so that it does not interfere with a surgical operation.

A description is given below of CABG using the graft grasping device of the present invention with reference to FIGS. 6 to 9.

Figure 6:
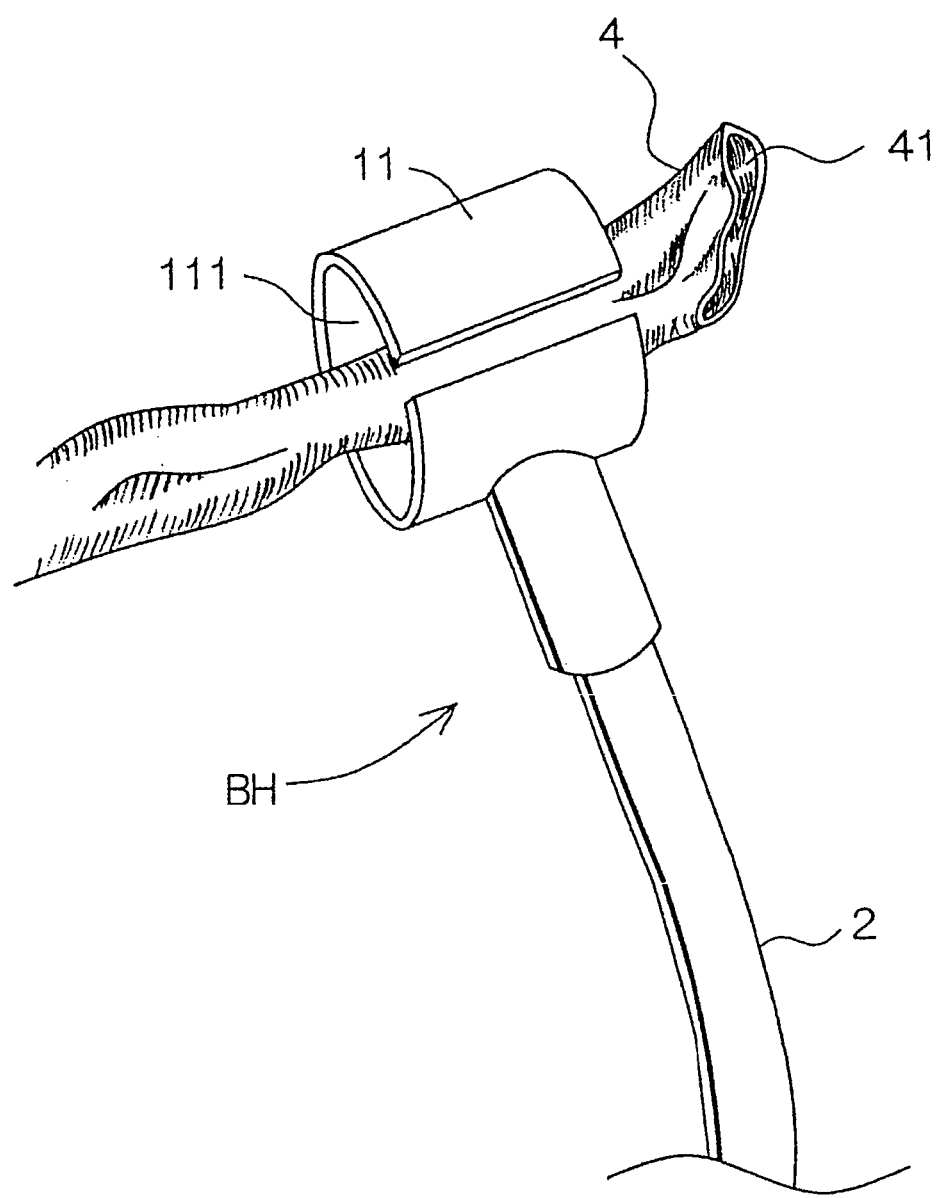
FIG. 6 is a diagram explaining a step of CABG using a graft grasping device of the present invention.
Figure 7:
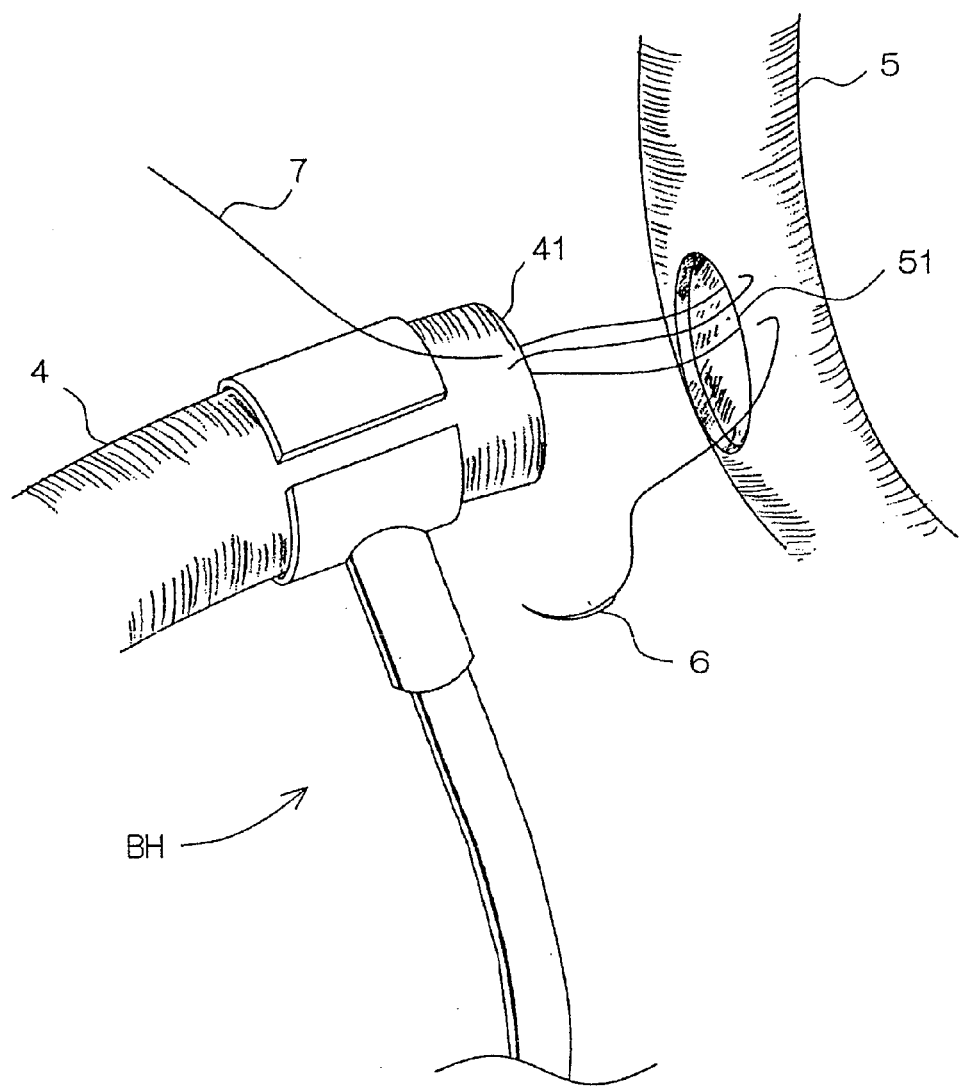
FIG. 7 is a diagram explaining a step of CABG using the graft grasping device of the present invention.
Figure 8:
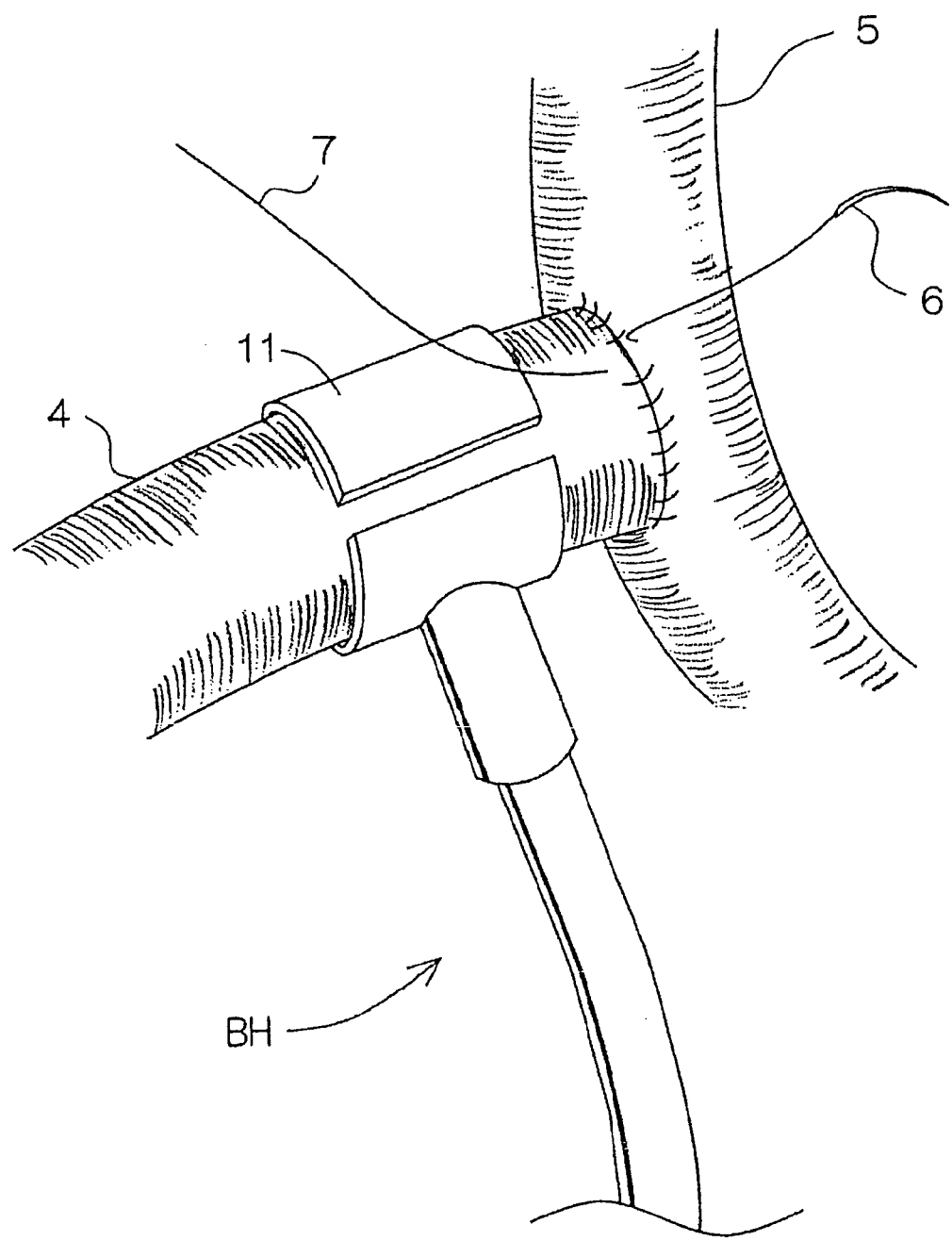
FIG. 8 is a diagram explaining a step of CABG using the graft grasping device of the present invention.
Figure 9:
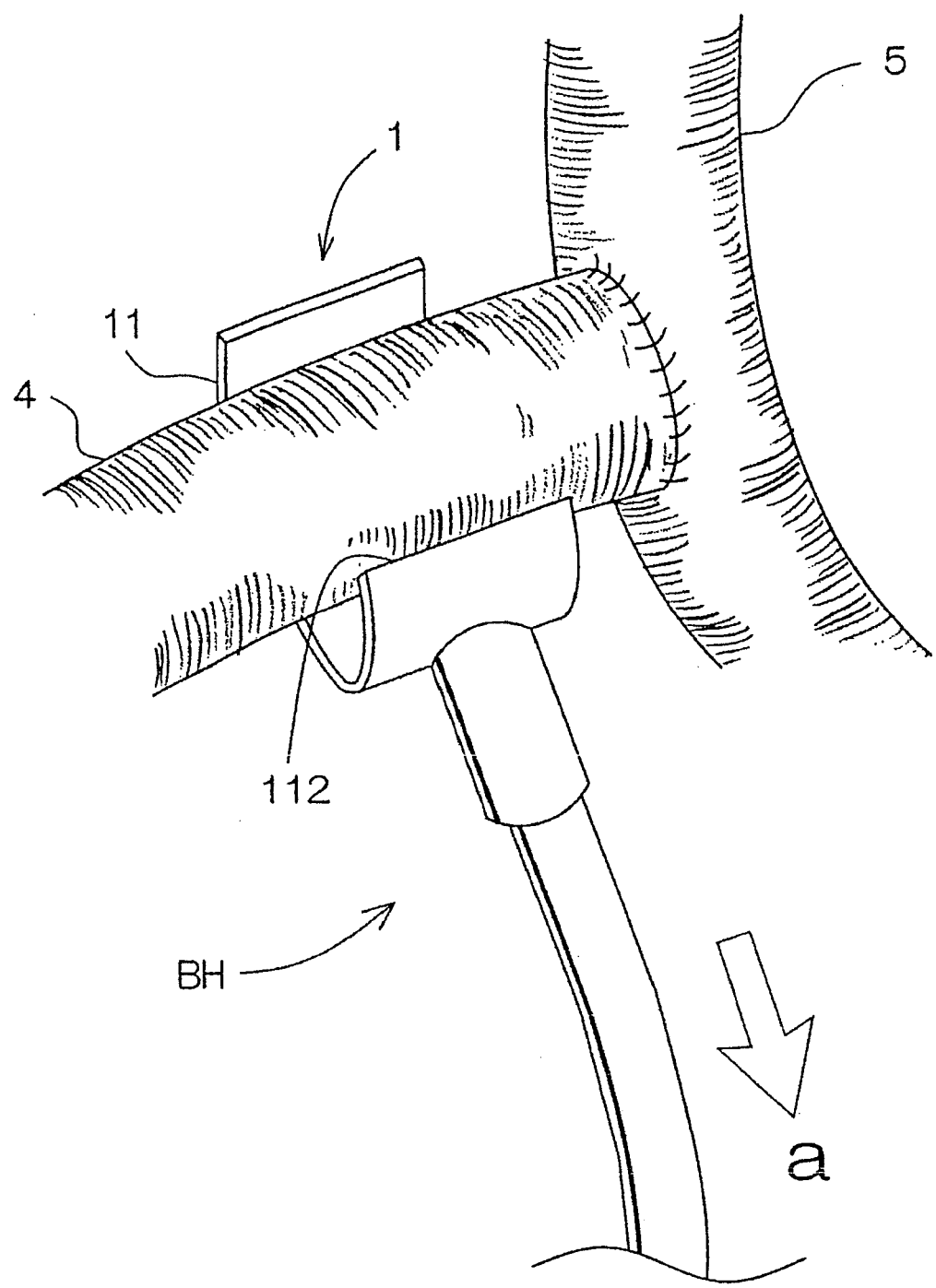
FIG. 9 a diagram explaining a step of CABG using the graft grasping device of the present invention.

First, the sternum is incised surgically to check the heart, after which a bypass graft (graft 4) is prepared. Thereafter, the anastomosing part of the coronary artery 5 which is seen on the surface of the heart is cut to make a hole 51 as shown in FIG. 7. Next, as shown in FIG. 6, the graft 4 is grasped by a graft grasping device BH and a negative pressure is applied to the lumen 111 of the grasping portion 11 by the suction device (not shown) connected to the suction tube 2. Then, the outer wall of the graft 4 is pulled, or sucked, against the porous sheet 13 by the negative pressure and the anastomosing port 41 is opened. In this state, the graft 4 is sutured with the coronary artery 5 using a suture needle 6 (see FIGS. 7 and 8). After the anastomosis, the slit 112 is opened by pulling the graft grasping device BH in a direction indicated by an arrow "a" in order to remove it from the graft 4. CABG is thus completed (see FIG. 9).

Figure 10:
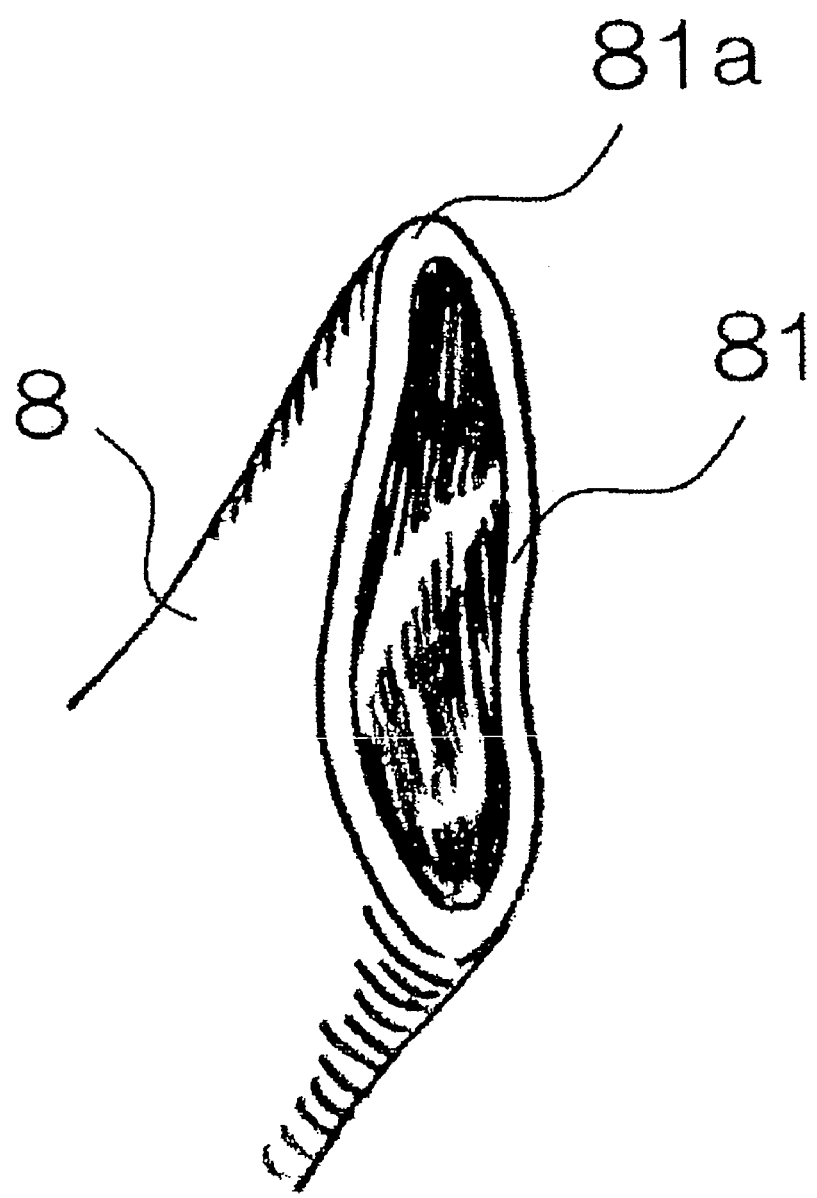
FIG. 10 a diagram showing how to cut a graft obliquely.
Figure 11:
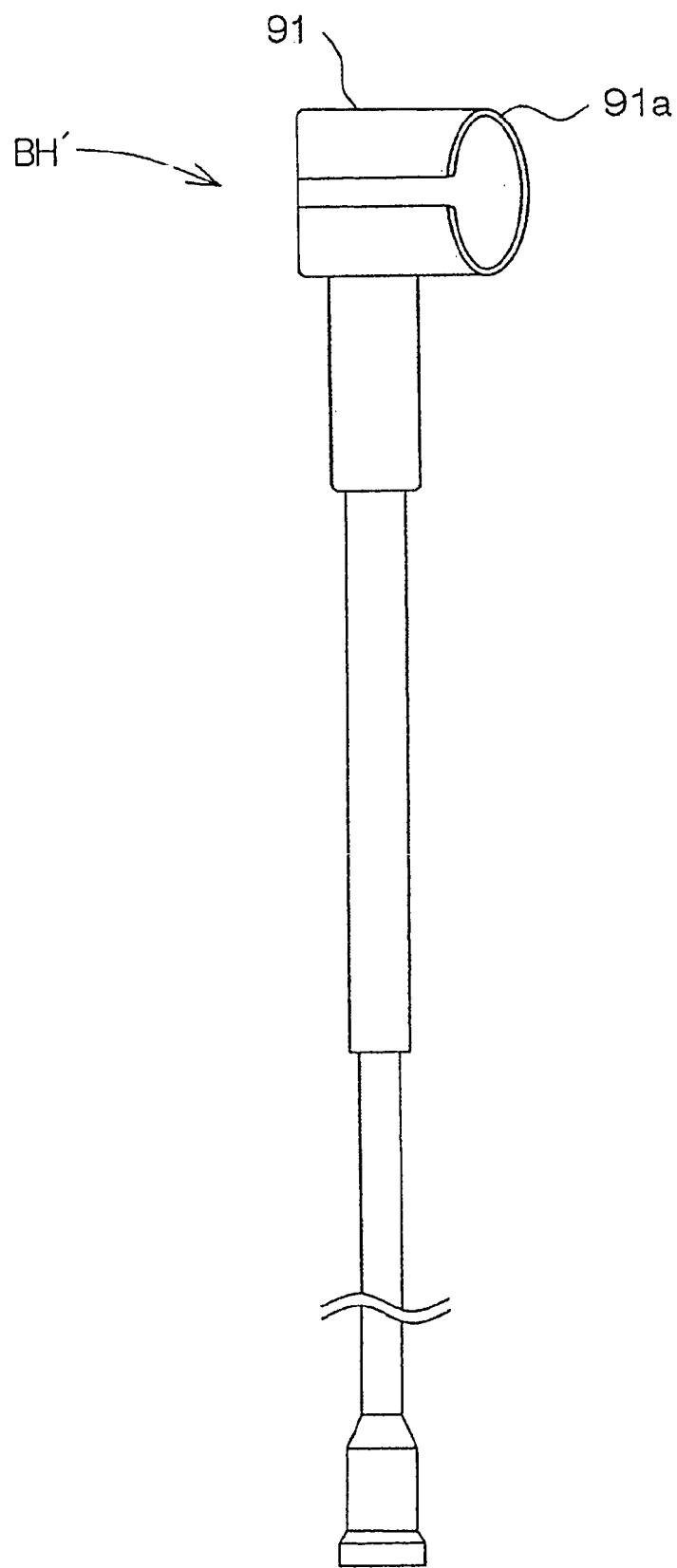
FIG. 11 a front view of another embodiment of the present invention.

Incidentally, the anastomosing port 41 shown in FIGS. 6 to 9 is formed perpendicular to the axial direction of the graft 4. However, at a clinical site, as shown in FIG. 10, an anastomosing port 81 is formed obliquely with respect to the axial direction of the graft 8 in most cases. In this way, when the anastomosing port 81 is formed like a smooth hood, its opening area becomes large and the amount of the running blood can be increased. However, when the graft 8 having the oblique anastomosing port 81 is grasped by the graft grasping device BH shown in FIGS. 1 to 5, the tip 81a of the anastomosing port 81 projects from the porous sheet 13, whereby it may be difficult to keep the anastomosing port 81 open. In this case, as shown in FIG. 11, a graft grasping device BH' having an inclined face 91a formed aslant with respect to the longitudinal direction of a grasping portion 91 is preferably used.

Figure 12:
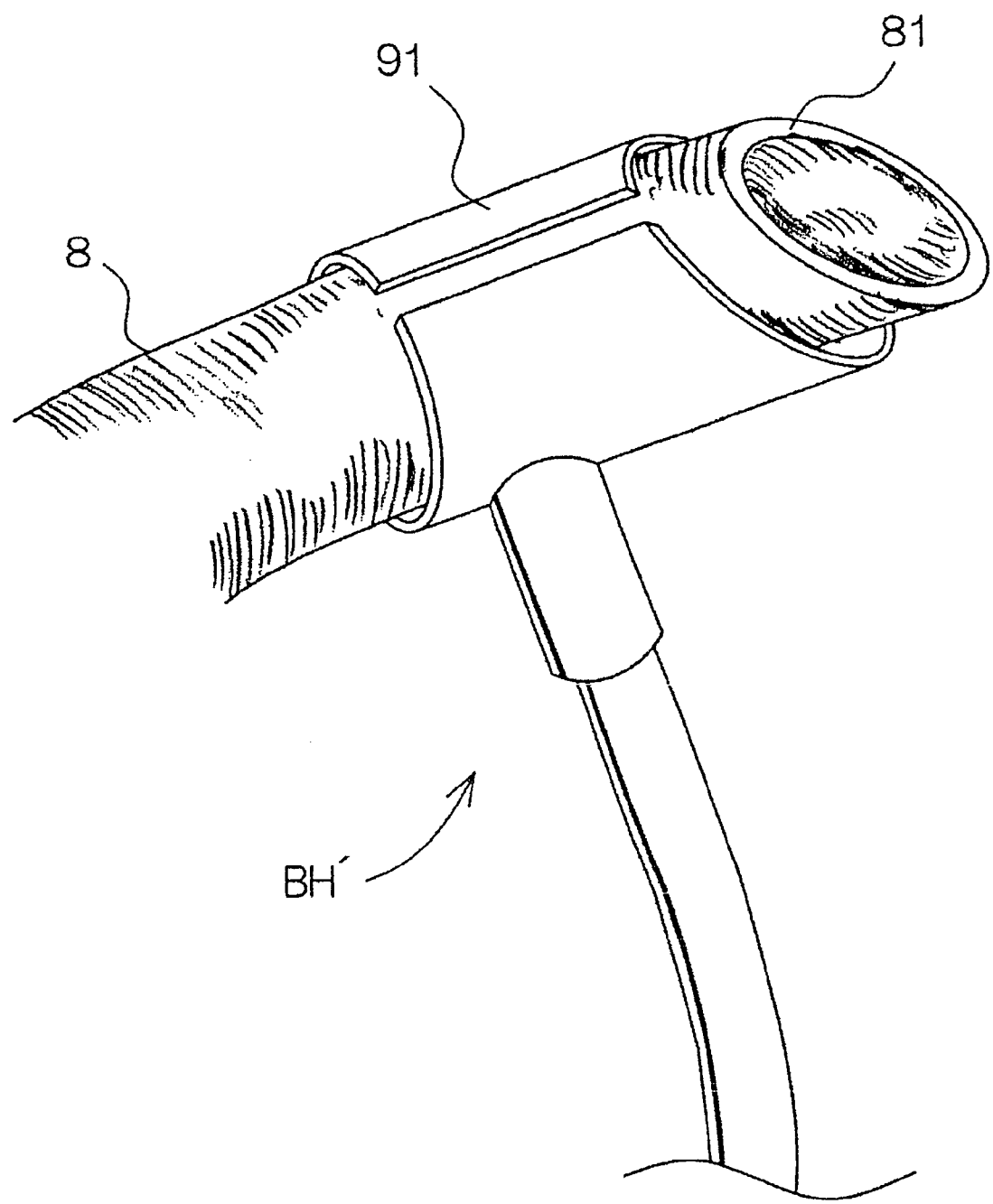
FIG. 12 a diagram explaining a use state of the graft grasping device of the present invention.

When the graft 8 is grasped by using the graft grasping device BH' in such a manner that the anastomosing port 81 and the inclined face 91a become substantially parallel to each other, it can be grasped while the anastomosing port 81 is open as shown in FIG. 12. In FIG. 11, only one end of the grasping portion 91 is formed obliquely but both ends may be formed obliquely. Note that the graft grasping device BH' having one end formed obliquely and the other end cut at a right angle as shown in FIG. 11 can be used for both a graft having an anastomosing port perpendicular to the axial direction of the graft and a graft having an oblique anastomosing port.

According to the present invention, a graft can be grasped by a graft grasping device making use of a suction force generated by negative pressure, thereby eliminating the fear that the intima of the graft is damaged, which is a problem to be solved in the method of the prior art using tweezers or the like. Further, the graft can be grasped while the anastomosing port of the graft is opened, thereby making it possible to anastomose grafts with each other reliably and easily. Particularly, the graft grasping device of the present invention can be advantageously used in CABG.

What is claimed is:

1. A graft grasping device comprising:
    a graft grasping portion in the shape of a cylindrical tube having a lumen and a slit formed in a longitudinal direction of the cylindrical tube such that said lumen has a C-shaped cross section; and
    a suction tube communicating with the lumen of the grasping portion for exerting a negative pressure in the lumen;
    an inner wall of the graft grasping portion having a recessed portion which communicates with a lumen of the suction tube, the recessed portion being covered with a sheet having a plurality of pores, and a mesh sheet being provided in a space defined between the recessed portion and the sheet.

2. A graft grasping device according to claim 1, further comprising a means for gripping the device.

3. A graft grasping device according to claim 2, wherein a suction tube connection portion is provided on an outer wall of the graft grasping portion and is connected to the suction tube and the means for gripping the device is connected to said suction tube connection portion concentrically to the suction tube.

4. A graft grasping device according to claim 1, wherein a connector is provided at a proximal end of the suction tube.

5. A graft grasping device comprising:
   a graft grasping portion in the shape of a cylindrical tube having a lumen and a slit formed in a longitudinal direction of the cylindrical tube such that said lumen has a C-shaped cross section; and
   a suction tube communicating with the lumen of the grasping portion for exerting a negative pressure in the lumen;
   an inner wall of the graft grasping portion having a recessed portion which communicates with a lumen of the suction tube, the recessed portion being covered with a sheet having a plurality of pores, and a mesh sheet being provided in a space defined between the recessed portion and the sheet, wherein said graft grasping portion has first and second longitudinal ends and the recessed portion is formed on the entire inner wall of the graft grafting portion excluding portions adjacent to said first and second longitudinal ends and portions adjacent to the slit.

6. A graft grasping device according to claim 5, wherein at least one of said longitudinal ends of the graft grasping portion is formed obliquely with respect to the longitudinal direction of the graft grasping portion.

7. A graft grasping device comprising:
   a graft grasping portion in the shape of a cylindrical tube having a lumen, a longitudinal axis, and a slit formed along the length of the tube parallel to the longitudinal axis of the tube such that said grasping portion has a C-shaped cross section perpendicular to the longitudinal axis of the tube; and
   a suction tube communicating with the lumen of the grasping portion for exerting a negative pressure in the lumen;
   an inner wall of the graft grasping portion having a recessed portion which communicates with a lumen of the suction tube, the recessed portion being covered with a sheet having a plurality of pores, and a mesh sheet being provided in a space defined between the recessed portion and the sheet.

* * * * *